United States Patent [19]

Emerson

[11] 4,353,358
[45] Oct. 12, 1982

[54] SIGMOIDOSCOPE

[76] Inventor: Reynolds L. Emerson, 116 Jefferson Rd., Webster Groves, Mo. 63119

[21] Appl. No.: 182,126

[22] Filed: Aug. 28, 1980

[51] Int. Cl.³ .............................................. A61B 1/00
[52] U.S. Cl. ..................................................... 128/4
[58] Field of Search ...................... 128/6, 4, 7, 3, 348, 128/349 R, 350 R

[56] References Cited

U.S. PATENT DOCUMENTS

| | | | |
|---|---|---|---|
| 3,044,461 | 7/1962 | Murdock | 128/4 |
| 3,266,059 | 8/1966 | Stelle | 128/4 X |
| 3,470,876 | 10/1969 | Barchilon | 128/4 X |
| 3,669,098 | 6/1972 | Takahashi | 128/6 |

FOREIGN PATENT DOCUMENTS 312350  5/1919  Fed. Rep. of Germany .......... 128/7

OTHER PUBLICATIONS

Recto-Colonic Endoscope, *Tiemann Catalog*, p. 300, 1889 Tiemann C., N.Y.

Disposable Sigmoidoscope, *Surgery, Gynecology & Obstetrics*, pp. 48-49.

*Primary Examiner*—Robert Peshock
*Assistant Examiner*—Mickey Yu
*Attorney, Agent, or Firm*—Haverstock, Garrett & Roberts

[57] ABSTRACT

An improved sigmoidoscope designed to be inserted into the rectum including a tubular member having opposite open ends with a passageway extending therebetween, an end portion of the tubular member being formed to be bendable as by weakening one side thereof to facilitate bending in a predetermined direction, an elongated flexible member attached to the tubular member adjacent the bendable end portions thereof and extending longitudinally along a portion of the length thereof, and an operator member attached to the elongated flexible member and movable to longitudinally displace the elongated flexible member to thereby apply sidewise bending motion to the bendable end portion of the tubular member. The device may optionally also include a cover layer extending over at least the bendable end portion thereof, and a grip to facilitate holding and manipulating the device.

35 Claims, 10 Drawing Figures

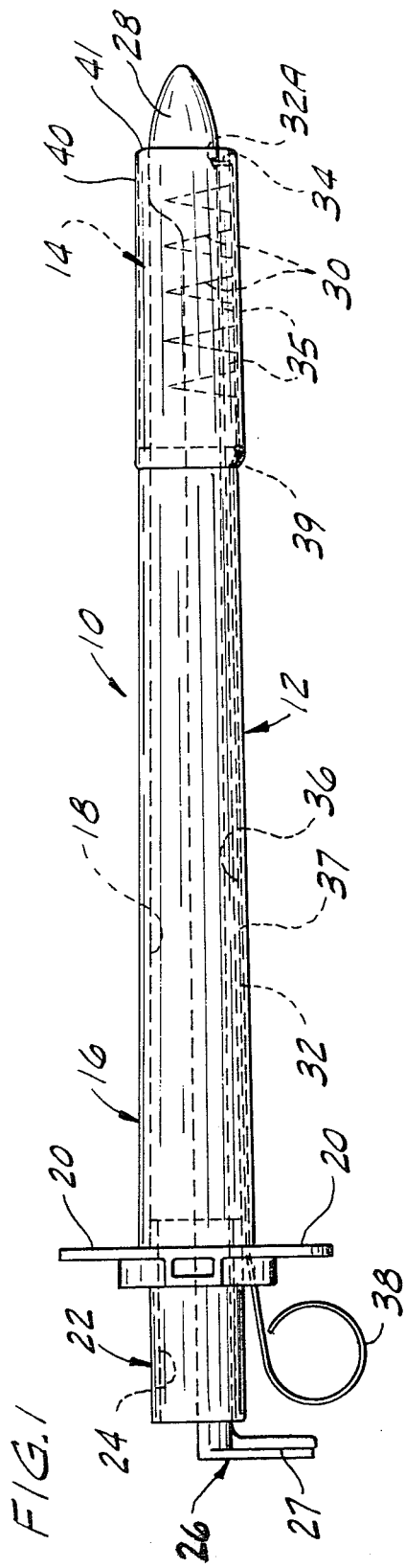
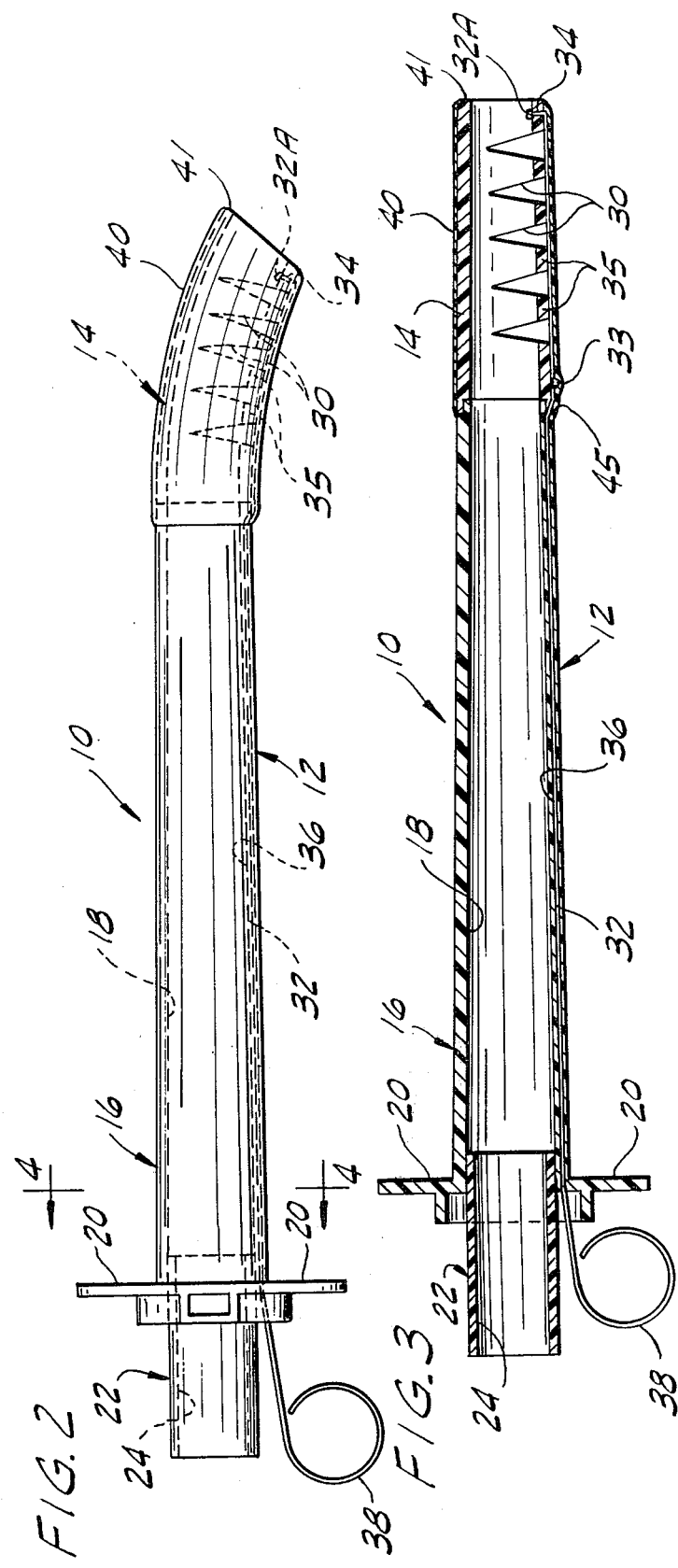

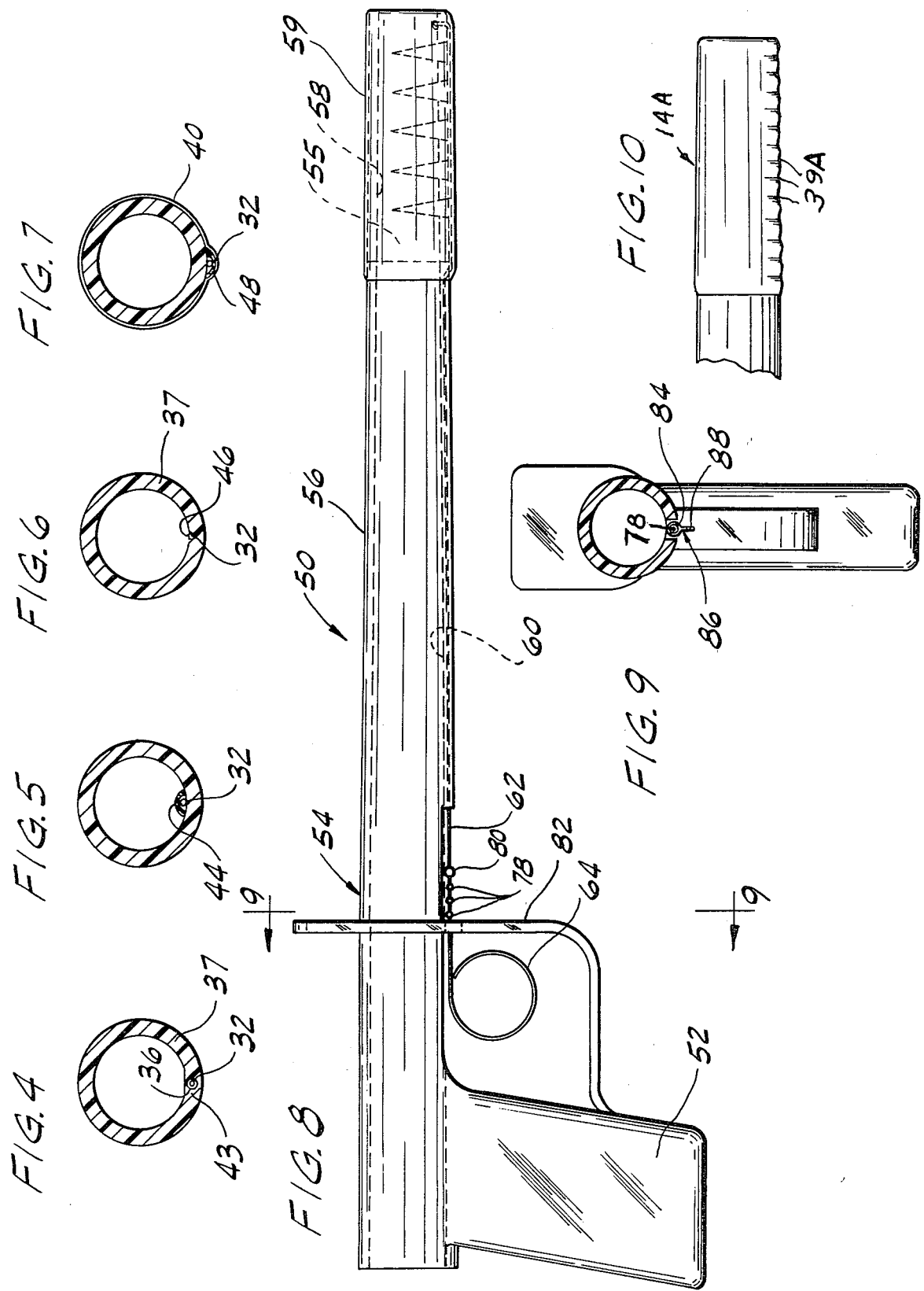

SIGMOIDOSCOPE

Sigmoidoscopes, some times also known as proctoscopes, are used for making rectal examinations, and such devices have been known for sometime and are used in clinics, labs, hospitals and in doctor's offices. Most prior art in this area, however, include relatively complicated sophisticated instruments which are designed primarily for clinical and hospital use. Typical examples of such devices are disclosed in U.S. Pat. Nos. 3,572,325; 3,610,231; 3,643,653; 3,788,304; 3,897,775; 3,948,251; 4,076,018; and 4,078,555. The known devices shown in these patents, though some have bendable flexible portions, are complicated and relatively costly, have been difficult and complicated to use, and have required maintainance and cleaning after each use which increases the expense involved in their use, and the known devices for the most part have not been disposable. The known devices also have obstructions which limit or interfere with optical inspection. There is also a relatively simple prior art device as disclosed in U.S. Pat. No. 3,417,746, but this device is rigid and non bendable and therefore suffers from many of the disadvantages which are overcome by the present improvements. The subject device is therefore an improvement over all known devices and is designed primarily for routine examinations, and is designed to be relatively inexpensive and disposable.

A sigmoidoscope or proctoscope, also sometimes known as an endoscope, is generally inserted a considerable distance into the rectum during rectal examinations, and in order to complete the insertion it is often necessary to apply some sideways guiding pressure especially against the forward tip area since the rectum is non linear and somewhat serpentine in shape. The guidance required during insertion can be very uncomfortable for the patient and can make the physician's or other operator's work more difficult and time consuming and this can also limit the examination. This is especially true if it is necessary, as is often the case, to guide the instrument around corners. Sigmoidoscopes which are designed for such examinations suffer from many such disadvantages, one of which is that they are generally not bendable, and accordingly their use is difficult and painful to the patient. As a result, full insertion is sometimes not achieved and visual examination of the full colon area is often incomplete. The present device is an improvement which enables the forward open ended inserted portion of the tubular member to be easily and accurately sidewardly deflected to some extent in a curved angular manner during insertion so as to enable the device to more easily follow the body cavity or rectum with minimum effort by the operator and with the least amount of discomfort to the patient. It is also important that this be accomplished without the operator losing the ability to sight through the device for examination purposes. Thus it is possible with the present device to obtain more thorough and more comfortable examinations. To accomplish this the side wall of the tube portion of the present device near the distal end thereof is weakened along one side such as by providing one or a series of cut outs or notches. A wire, flexible member or cord is provided which is connected at one end near to the weakened portion adjacent to the distal end and at the opposite end to an operator member or trigger which when actuated pulls on the distal end to curve or bend the end portion in a sidewardly direction and to the extent desired to facilitate insertion but without loss of vision through the device. This simple manner of constructing and controlling the bending of the bendable end portion of the proctoscope allows the device to be accurately and easily guided during insertion, with less discomfort to the patient and the subject improvements can be embodied in a known type device such as in the device disclosed in U.S. Pat. No. 3,417,746 without substantially increasing the cost thereof and without losing the advantage it enjoys of being disposable. Thus, the subject construction provides advantages over known sigmoidoscopes and especially those used in rectal examinations which heretofore have been relatively rigid, non-bendable and therefore difficult and uncomfortable to use.

It is therefore a principal object of the present invention to provide an improved sigmoidoscope particularly for use in making rectal examinations.

Another object is to provide a relatively inexpensive sigmoidoscope.

Another advantage is to teach the construction and operation of a relatively simple sigmoidoscope device which has a bendable end portion, which device is simple to insert, guide and use and less painful for the patient.

Yet another advantage is to provide an improved yet disposable sigmoidoscope.

Another object is to enable a doctor or other person inserting a sigmoidoscope to be able at all times to maintain good visual contact with the rectal areas through the device while at the same time being able to sidewardly deflect the inserted end portion of the device to some extent to facilitate insertion even along relatively nonlinear areas.

Another advantage is to make it easier and more comfortable to insert a sigmoidoscope into the rectum of a patient.

Another advantage is to improve the quality of proctoscopic examinations.

Another object is to provide a sigmoidoscope which can be manipulated more easily and to a greater extent than prior devices during insertion thereby to increase the area examined.

These and other objects and advantages of the present invention will become apparent after considering the following detailed specification in conjunction with the accompanying drawings, wherein:

FIG. 1 is a side elevational view of the present improved sigmoidoscope in condition to be inserted;

FIG. 2 is a side elevational view of the same device with the obturator removed and showing the end portion of the device in a sidewardly deflected condition;

FIG. 3 is a cross sectional view taken along the axis of the device of FIG. 1 showing the device with the obturator removed;

FIG. 4 is a cross sectional view taken on line 4—4 of FIG. 2;

FIG. 5 is a cross sectional view similar to FIG. 4, showing an alternate embodiment of the device;

FIG. 6 is a cross sectional view similar to FIG. 4 showing another alternate embodiment of the device;

FIG. 7 is a cross sectional view similar to FIG. 4 showing yet another embodiment;

FIG. 8 is a side elevational view showing an embodiment of the device provided with a hand grip;

FIG. 9 is a cross-sectional view showing the details of a latch means useful to maintain a particular angular deflection for the leading end portion of the present device, taken on line 9—9 in FIG. 8; and FIG. 10 is a fragmentary side view showing another embodiment of the bendable end portion of the device.

Referring to the drawings more particularly by reference numbers, number 10 refers to a sigmoidoscope which includes the improvements of the present invention. The device 10 has a tubular endoscope portion 12 which extends between opposite end portions 14 and 16 and a passageway 18 extends through the device. The tubular member 12 in the preferred embodiment is slightly conical or tapered from end-to-end such that the forward end portion 14 has a diameter slightly less than that of rear end portion 16, though this is not essential. The tube 12 may be constructed of a variety of materials, but a preferred material is a plastic material which is relatively inexpensive and can be easily and inexpensively molded so as to make the device cheap enough to be disposable. The rear or operator end portion 16 of the member 12 has opposite sidewardly extending flanges or handle members 20 which are integral therewith and are useful in handling and manipulating the device during insertion and inspection. The operator end 16 of the tube 12 is also connected to a rearwardly extending concentric tubular portion 22, which is press fitted therein and has a tubular passageway 24 therethrough that is somewhat smaller than the passageway 18 and serves as an extension of passageway 18. The member or portion 22 is constructed to accommodate a suitable light source and/or optical means (not shown) which are not part of the present invention as such. Prior to rectal insertion of the present device an obturator member 26 is positioned extending through the passageways 18 and 24 as shown in FIG. 1, and the obturator 26 is provided to facilitate initial insertion of the device into a body cavity such as into the rectal opening. The obturator 26 has a handle portion 27 and a rounded forward end portion 28 which extends beyond the forward end portion 14 of the member 12 when installed to facilitate this purpose. The obturator 26 is assembled and positioned as shown in FIG. 1, and after initial insertion the obturator 26 is withdrawn and is no longer used. Thereafter, further insertion is accomplished in a manner which will be explained. The construction and operation of the present device is somewhat similar to that of the construction shown in U.S. Pat. No. 3,417,746, but the present device includes substantial improvements to the known construction which may be incorporated into the known device with little additional cost and modification.

The front or free end portion 14 of tubular member 12 in the present device is weakened along one side as by providing one or more aligned cutouts or notches 30 or by otherwise weakening the member on the side as by making the side thinner. In the preferred embodiment the free end portion 14 is formed as a continuous extension of tubular member 12, but it may be constructed as a separate end piece which is threadedly or otherwise engageable with the tubular member 12.

An operator cord member such as wire, plastic or string member 32 is attached to the portion 14 adjacent to the distal or free end thereof as at 34 and possibly also to one side of the segments 35 which extend between the adjacent cutouts 30. In the preferred embodiment, the cord member 32 extends longitudinally along the outer surface of the segments 35 although it can also extend on the inside of the segments 35 or even through the segments or through the weakened side of the device. Thereafter the cord 32 extends along the length of tube 12 preferrably through a bore 36 formed in the wall 37 thereof. The cord 32 is attached adjacent to the operator end 16 of the tube 12 to an operator member such as trigger 38 which may be a separate member or a curved portion of the cord or wire itself. During insertion of the device 10, the trigger 38, which should be spaced far enough away from the member 22 to accommodate the placement of the optics and light source after removal of the obturator 26, is pulled by the operator's finger to tension the cord 32. This in turn causes some pulling on, and resulting bending of, the bendable end portion 14 at the location of cutouts 30, or weakened side area, thereby enabling the end portion 14 of the tube 12 to be bent sidewardly to conform to and to therefore more easily follow the shape of the body cavity or rectum into which the device is inserted. Since the rectum is somewhat serpentine in shape, as are many body cavities, it is highly desireable to be able to guide the proctoscope around corners as easily as possible, and this is greatly facilitated by the ability of the leading end portion 14 of the device to be able to be bent under control of the operator during insertion. It should be noted, however, that the distal or leading end portion 14 may be made to be bendable in many different ways, such as by providing the cutouts 30, by providing accordion type folds 39 (FIG. 10) in end portion 14A, or by weakening or thinning the end portion along one side, or by constructing one side of the tube of a more flexible material than that of the opposite side, and the present invention is deemed to cover all such embodiments. Although the end portion 14 must be bendable, it must also be of sufficient rigidity to retain its round shape even when bent so that it will not collapse and will enable rectal examination during insertion and withdrawal. The end portions 14 can be made as an integral part of the member 12 and it can also be made as an attachment thereto in which case a more flexible material may be used. It is preferred, however, to have it integral so that there will not be any ridge or other roughness where the members are connected.

The tube 12 may also be constructed so that the end portion 14 can be bent and made to retain a predetermined bent condition even when no operator's force is applied to the trigger, and the end portion should also preferrably be able to straighten itself out by its own resiliency or by the operator applying sideward pressure thereto. Such a construction may be desireable both during insertion and after the device is fully inserted so that the device will be able to retain a predetermined bend even without the operator having to apply pressure to the trigger. The maximum possible bend in the tube should preferrably never be so great that the operator can not at all times see completely through the device to make his examination during insertion as well as when the device is fully or partially inserted. The present improvements make this possible.

The sigmoidoscope 10 is also preferrably provided with a protective outer layer or sheath 40 which extends to cover the part of the tubular member 12 at the location of cut-outs 30 when cut-outs are used to weaken the device. The sheath 40 reduces resistance to movement which might be caused by the cut-outs 30 and/or possible discomfort to the patient during the insertion and withdrawal, and the sheath 40 also prevents materials from entering the side of the device through the cut-outs 30 which could adversely affect visual inspection during examinations. The sheath 40 may be made of various materials including preferably a thin flexible plastic material. Further, the sheath 40 may extend the entire length of the tubular member 12, which is desireable in some embodiments as will be explained, but, in the embodiment that has cut-outs 30 it should extend at least over the area of the cut-outs 30 at the forward end of the device for the reasons stated. In embodiments where the end portion of the device is weakened along one side or has accoridan means on one side as in the construction of FIG. 10 no sheath will generally be required.

As previously mentioned, the cord 32 extends along most of the length of the tubular member 12 and over much of its length extends through the bore 36 provided therefor in the wall 37 thereof as well as preferably, though not necessarily, across the outer surface of the device at the location of the cut-outs 30, where the cord 32 extends along the outside of the tube and beneath the sheath 40. The free end 32A of the cord 32 if made of wire is formed into a hook or bead and is attached to the tube adjacent to the distal or free end thereof. In this way the cord 32 is contained within the structure of the device over most, if not all its length, and is not able to come in contact with the patient or obstruct the view through the tube, even when the forward end portion 14 of the tube is bent. Also the cord 32 is so positioned and located so as not to interfere with or obstruct the use of the obturator 26. The construction therefore provides a smooth relatively uninterrupted path for the cord 32 and reduces resistance when the cord is pulled thus facilitating operation of the device. When the bore 36 through which the cord 32 extends is formed in the wall 37 of the tube 12 the wall 37 can be made to be somewhat thicker as at 43 (FIG. 4) to accommodate the cord 32 or other means may be used as will be explained in connection with FIGS. 5-7 for example. The enlarged tube portion 43 as shown in FIG. 4 may reduce to some extent the size of the passageway 18 but this is usually not objectionable so long as the obturator 26 can be used and is preferable to forming a ridge on the outer surface of the tube 12 to accommodate the cord 32 because an outside ridge can cause some discomfort to the patient especially if the device is rotated after being inserted. Alternatively, the cord 32 may extend along the inner surface of the passageway 18, and suitable guide members such as eyelets 44 shown in FIG. 5 may be provided if necessary. Alternatively, or in addition, as shown in FIG. 6, the wall member 37 of the tube 12 may be provided with an elongated notch or groove 46 formed on the inner surface thereof to accommodate and guide the cord 32. Still further, the cord 32 may extend along the outside of the tube 12 but within the sheath 40, and may be held in proper alignment by the combination of the sheath 40 and one or more smooth surfaced eyelets such as eyelets 48 as shown in FIG. 7. Other means for locating and supporting the cord member 32 may also be used so long as they accomplish the intended purpose. When the cord 32 is to be positioned between the tube 12 and the sheath 40, the sheath should preferably extend most of the length of tube 12 to prevent the cord from coming in direct contact with and rubbing on the flesh of the patient. The eyelet 48 may also be substituted for by a bore (not shown) formed in handle or grip members 20 at the appropriate location.

It should also be noted that member 32 may be attached to the tube 12 in a number of different manners at the location 34, (FIG. 1), and may also be directed upwardly and attached at alternate location 41, on the opposite side of tubular member 12 from notches 30. If this is done it will limit the amount that the end portion can deflect which may be desireable, but it may cause some optical interference with vision and may make it more difficult to use the device with the obturator 26. If the member 32 is to be attached at location 41, it may be necessary that the member 32 pass through a bore such as the bore 36, or through an eyelet located approximately at the position 39 (FIG. 1) which is just behind where the cutouts 30 are located.

The cord member 32 may be made of many different materials including plastic, thread, string, cord, or wire, and it must be strong enough to do the job and cheap enough not to add substantially to the cost of the device. Wire is usually the best choice for the member 32. Wire, like piano-wire, has a rigidity which will enable the operator to straighten the end curve of the proctoscope at will by pressing forward on the trigger thus eliminating the need for uncomfortable sideways pressure on the end of the scope, against the bowel wall, in order to straighten the curve.

Shown in FIG. 8 is a modified form of proctoscope 50 which is provided with a grip member 52, similar to a pistol grip, which is made integral with operator end 54 of tubular member 56. As so constructed, the device 50 may be even more firmly held and manipulated by the operator, and guided into position while the operator is making his visual examination through opening 58 of tubular extension 59 which is an extension of passageway 60 in the tubular member 56. Once the device is initially inserted and the obturator withdrawn, the operator may easily and conveniently complete the insertion while looking through the opening 58 and the passageway 60 to make the necessary observations and to direct the bending as the device progresses into the body cavity. The grip member 52 provides good support for the operator as he manipulates the device into positions during insertion. The device 50 is constructed, as are the other embodiments, to assure its ease of operation and to minimize the discomfort experienced by the patient during an insertion process.

It is important to the present invention that the operator always be able to view the body cavity through the subject sigmoidoscope, even when the end portion is deflected, as aforesaid, and thus it may be desireable to provide means to limit the amount of possible deflection to insure that the tube is never bent so far as to prevent viewing. In this regard, as shown in FIG. 3, the cord member 32 is provided with an optional bead or other stop means such as bead 33, (or 80) which, upon actuation of the cord 32 by means of the trigger 38, will move into contact with an abutment 45 after the end portion 14 has been deflected to some predetermined maximum possible deflection. This should preferably occur at some point not exceeding the condition whereby it is still possible to see completely through the device. The abutment 45, is shown formed by the end of the bore 36, and, thus, the bead 33 should be of a greater diameter than that of the bore 36. Also, the distance between the bead 33 and the abutment 45 should be such that when the operator member or trigger 38 (or 64) is actuated, movement of the cord will be limited by movement of the bead 33 into engagement with the abutment 45. This will control and limit the amount of possible deflection of the end portion 14 (or 55) of the tube 12. It is usually preferred, as indicated, that the maximum possible deflection never be so great as to prevent visual observation through the tube from end-to-end.

The modified embodiment shown in FIG. 8 includes means to maintain a predetermined bend in the end portion 55. This embodiment includes a plurality of small spaced beads 78 and a larger bead 80, all located on the cord 62 adjacent to the handle end of the device in position so that they will move relative to a fixed wall or trigger guard 82 which extends around the trigger 64. When the trigger 64 is actuated to bend the end portion 55, the beads 78 will move through an enlarged opening portion 84 of opening 86 (FIG. 9) until the desired amount of bend of the end portion 55 is obtained. Thereafter the trigger can be moved downwardly to move a selected one of the beads 78 in line with a narrower opening portion 88 so that when the trigger 64 is released the bead 78 adjacent the opening portion 88 will be prevented from moving back through the opening 86 to retain the desired bent condition for the end portion 55. The larger opening portion 84 is large enough to allow the smaller adjustment beads 78 to pass but is too small to permit passage of the larger bead 80 which serves to limit the amount of possible bend that can be achieved. It should be noted that the doctor or other operator can take his hand off the trigger mechanism 64 when one of the beads 78 is locked in position by the narrow opening portion 88, and this will free the doctor from having to maintain pressure on the trigger 64 in order to bend the tube end portion 55. Any of the beads 78 can be trapped in the narrow opening portion 88 depending on the desired amount of tube deflection to be maintained. The beads 78 and 80 can be formed by knots tied in the cord 62 or by attaching separate bead members thereto.

In order to operate any of the disclosed embodiments of the subject device the operator or physician places the obturator 26 into the position as shown in FIG. 1, and makes the initial insertion of the end portion 28 into the rectal passageway. When suitable penetration has been made, the obturator 26 will be withdrawn from the device and suitable optical means (not shown) will be attached to enable completion of rectal examination. With the optics in place the device will be gradually further inserted, and during insertion optical examination and inspection will take place. As the device is inserted it will usually encounter non-linear portions of the rectal cavity and at these times the doctor will be able to manipulate the trigger 38 or 64 in order to deflect the end portion 14 (or 55) and he may lock the end portion in a particular deflected position if means such as are described in connection with FIG. 8 and FIG. 9 are provided. This procedure continues until the device has been inserted to the desired depth. The examination may continue during insertion of the device as well as during withdrawal, and after the examination is over the optical equipment can be detached so that the inserted portions including the obturator 26 can be discarded or resterilized for later use. In the usual situation it is expected that the device will be discarded.

Thus there has been shown and described an improved sigmoidoscope which fulfills all of the objects and advantages sought therefor. It will become apparent to those skilled in the art, however, that many changes, modifications, alterations, and other uses and applications of the subject device are possible, and all such changes, modifications, alterations, and other uses and applications that do not depart from the spirit and scope of the invention are deemed to be covered by the invention which is limited only by the claims which follow.

What is claimed is:

1. A proctoscope comprising an elongated open ended tubular member of unitary construction having opposite first and second ends with adjacent end portions and a passageway extending between said first and second ends through the device, one of said end portions being constructed to be bendable primarily in one direction, a relatively stiff cord member having a first end connected to the tubular member adjacent to said first tube end, the cord member extending along the tubular member on the side thereof in which said one end portion is bendable to adjacent the second tube end, and operator means connected to the cord member adjacent to the second tube end, said operator means being movable between an inoperative position in which said one bendable tube end portion is substantially in alignment with the rest of the tubular member and an operative position whereby the cord member is pulled toward the second tube end and is moved longitudinally relative to the tubular member to pull on and deflect said one bendable end portion sidewardly in said one direction relative to the tubular member, said operator means and said tubular member including means that are engageable during longitudinal movement of the cord member to limit deflection of the bendable end portion such that visual examination can be made completely through said tubular member in all positions of the operator member.

2. The proctoscope defined in claim 1 wherein said bendable tube end portion includes means along one side thereof weakening said one side to facilitate sideward bending thereof.

3. The proctoscope defined in claim 1 wherein said bendable tube end portion has at least one segmentally shaped cut out formed extending inwardly from the side thereof to facilitate bending thereof.

4. The proctoscope defined in claim 1 including an outer covering member extending over the bendable tube end portion.

5. The proctoscope defined in claim 1 including grip means attached to the tubular member adjacent to the tube end portion opposite from the bendable end portion to facilitate manual control and movement thereof.

6. The proctoscope defined in claim 1 wherein said bendable tube end portion includes a plurality of accordion shaped folds formed extending along at least one side thereof.

7. The proctoscope defined in claim 1 wherein the cord member is formed of wire.

8. The proctoscope defined in claim 1 wherein the cord member is formed of a string-like material.

9. The proctoscope defined in claim 1 wherein the cord member is formed of plastic.

10. The proctoscope defined in claim 1 wherein the tubular member includes a wall with a longitudinally extending bore formed therein to accommodate a portion of the length of the cord member therein.

11. The proctoscope defined in claim 1 wherein said operator means includes a finger grip member attached to said cord member.

12. The proctoscope defined in claim 1 including guide means located within the passageway through said tubular member for accommodating and movably supporting the cord member.

13. The proctoscope defined in claim 1 wherein said deflection limiting means include an abutment surface formed on the tubular member adjacent to the cord member, and stop means attached to the cord member for movement into engagement with the abutment surface in a preselected position of the cord member to limit the amount of possible bending of the bendable tube end portion.

14. The proctoscope defined in claim 13 wherein said stop means includes an enlargement on the cord member, a cord opening in the tubular member through which the cord member extends, said abutment surface extending to adjacent the cord opening, said enlargement being too large to pass the abutment surface to enter the cord opening.

15. The proctoscope defined in claim 14 wherein said enlargement includes a bead member attached to said cord member.

16. The proctoscope defined in claim 14 wherein said enlargement includes a knot tied in the cord member.

17. A disposable instrument for examining a body cavity comprising an elongated open ended tubular member of unitary construction with opposite first and second end portions extending between corresponding first and second tube ends, a passageway extending through the tubular member between said end portions, the first end portion having means along at least one side thereof weakening said first end portion therealong to make the first end portion relatively more bendable than the rest of the tubular member, means to controllably bend or straighten said first tube end portion, said means including an elongated relatively stiff cord member having a first end connected to said first end portion adjacent to the first tube end, a second cord end portion extending to adjacent to the second tube end portion, a portion of the cord member extending therebetween along the tubular member on the side thereof where the first end portion is weakened, and operator means attached to the second cord end portion, said operator means including the cord member being movable between an inoperative position in which the first end portion of the tubular member is a substantially aligned position with the rest of the tubular member and an operative position whereby the operator member is pulled and moves the cord member longitudinally relative to the tubular member thereby angularly and laterally deflecting the first tube end portion relative to the rest of the tubular member, said operator means and said tubular member including cooperatively engagable means thereon in position to become engaged to limit deflection of the first end portion such that visual inspection can be made completely through the tubular member in all positions of the operator member.

18. The instrument defined in claim 17 including an outer cover member extending over the first tube end portion.

19. The instrument defined in claim 17 including grip means for manipulating the instrument, said grip means being attached to the tubular member adjacent to the second end portion thereof and being shaped to fit the hand.

20. The instrument defined in claim 17 wherein said bendable first tube end portion includes at least one cut out segment formed extending inwardly from said one side thereof.

21. The instrument defined in claim 17 wherein a plurality of spaced aligned cut out segments are formed in said one side of the first tube end portion.

22. The instrument defined in claim 17 wherein said cord member extends along the length of said tubular member on the one side thereof where the first end portion is weakened.

23. The instrument defined in claim 17 including a longitudinally extending bore formed in the wall of said tubular member, said cord member extending through said bore.

24. The instrument defined in claim 17 wherein at least a portion of the cord member extends through said passageway in the tubular member, said tubular member having at least one guide member located in said passageway to support and guide the cord member.

25. The instrument defined in claim 17 wherein said operator means includes a loop formed by the cord member adjacent to the second end portion thereof.

26. The instrument defined in claim 17 wherein said deflection limiting means include stop means on the cord member and an abutment formed on the tubular member and engagable by the stop means during operation of the operator means to limit the amount of possible bending of the first tube end portion.

27. The instrument defined in claim 26 wherein said stop means includes a bead attached to said cord member, the abutment including a wall member on the tubular member with an orifice therethrough through which said cord member extends.

28. The instrument defined in claim 26 wherein the stop means includes a plurality of beads attached to the cord member at spaced locations therealong, and the abutment includes a wall member having an orifice therethrough through which the cord member extends, said orifice having a first orifice portion large enough for the beads to pass through and a second connected orifice portion through which the beads will not pass.

29. The instrument defined in claim 26 wherein the stop means includes a knot tied in the cord member.

30. The instrument defined in claim 28 wherein one of said beads on the cord member is too large to pass through the orifice thereby limiting the amount of possible movement of the cord member.

31. The instrument defined in claim 17 wherein the cord member is a wire member.

32. The instrument defined in claim 17 wherein the cord member is formed of a plastic material.

33. A sigmoidoscope instrument for use in making rectal examinations comprising an elongated open ended tubular member of unitary construction having leading and trailing ends and a leading end portion which extends from the leading end and is the portion that is first inserted during an examination, means weakening the leading end portion along at least a portion of one side thereof enabling the leading end portion to be controllably sidewardly deflected along a curved path as an aid to guiding the instrument during insertion, and operator means including an operator member under control of the operator of the instrument to effect predetermined sideward and curved deflection of the leading end portion, said operator means including a relatively stiff cord member being capable of producing pushing and pulling force extending longitudinally along the tubular member on the side thereof where the leading end portion is weakened, said cord member having a first end connected adjacent to the leading end of the tubular member and a second opposite end connected to the operator member, said cord member being movable longitudinally of the tube when the operator member is pulled to sidewardly deflect and curve the leading end portion of the tubular member and when the operator member is pushed to be stiff enough to straighten out the leading end portion of the tubular member.

34. A proctoscope comprising a tubular member having opposite ends with respective adjacent first and second end portions, a passageway extending through the device between the opposite ends, the first end portion having at least one segmentally shaped cutout segment extending inwardly from the side thereof to enable it to be deflected sidewardly along a curved path, an operator member adjacent to the second end portion, adjustment means under control of the operator member including a relatively stiff cord member having opposite end portions, one of which is attached to said deflectable first tube end portion adjacent to the tube end and extending along the tubular member on the side of the segmentally shaped cutout segment to adjacent the opposite tube end, the opposite end of the cord member being connected to the operator member, said operator member being movable between an inoperative position wherein said cord member is stiff enough to maintain the first tube end portion in substantial alignment with the rest of the tubular member and an operative position wherein the cord member pulls on and sidwardly deflects and curves the first tube end portion, and cooperatively engagable means on the cord member and the tubular member to limit relative movement therebetween to thereby limit the curved deflection of the first tube end portion so that visual inspection can be made through said tubular member in all positions of the operator member.

35. The proctoscope of claim 34 including cooperatively engageable means on the cord member and on the tubular member to maintain the cord member in a predetermined operative position relative to the tubular member in order to maintain a predetermined deflected position of the first tube end portion.

* * * * *